United States Patent
Nishida et al.

(10) Patent No.: US 10,545,143 B2
(45) Date of Patent: Jan. 28, 2020

(54) SILICA PARTICLES HAVING REACTIVE FUNCTIONAL GROUP ON SURFACE, AND METHOD OF PRODUCING THE SAME

(71) Applicant: FURUKAWA ELECTRIC CO., LTD., Tokyo (JP)

(72) Inventors: Masataka Nishida, Tokyo (JP); Nobumitsu Yamanaka, Tokyo (JP); Kazutomi Miyoshi, Tokyo (JP); Michio Ohkubo, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 130 days.

(21) Appl. No.: 15/016,028

(22) Filed: Feb. 4, 2016

(65) Prior Publication Data

US 2016/0153981 A1 Jun. 2, 2016

Related U.S. Application Data

(63) Continuation of application No. PCT/JP2014/070996, filed on Aug. 8, 2014.

(30) Foreign Application Priority Data

Aug. 12, 2013 (JP) .................................. 2013-167902

(51) Int. Cl.
*G01N 33/552* (2006.01)
*G01N 33/58* (2006.01)

(52) U.S. Cl.
CPC ......... *G01N 33/552* (2013.01); *G01N 33/582* (2013.01)

(58) Field of Classification Search
CPC ........... G01N 33/54353; G01N 33/552; G01N 33/582
See application file for complete search history.

(56) References Cited

U.S. PATENT DOCUMENTS

| | | | | |
|---|---|---|---|---|
| 8,796,040 B2* | 8/2014 | Aizawa | ............... | G01N 15/1459 422/73 |
| 8,993,345 B2* | 3/2015 | Aizawa | ............ | G01N 33/54346 436/172 |
| 9,260,656 B2* | 2/2016 | Aizawa | ................. | C09B 68/443 |
| 2008/0293584 A1* | 11/2008 | Aizawa | ................. | B82Y 30/00 506/9 |
| 2009/0068639 A1* | 3/2009 | Aizawa | .............. | G01N 15/1459 435/5 |
| 2011/0020241 A1 | 1/2011 | Tsukada et al. | | |
| 2014/0051186 A1 | 2/2014 | Aizawa et al. | | |
| 2015/0338395 A1* | 11/2015 | Yamanaka | ........... | G01N 33/552 436/501 |

FOREIGN PATENT DOCUMENTS

| | | |
|---|---|---|
| JP | 2010-100542 A | 5/2010 |
| JP | 2011-225381 A | 11/2011 |
| WO | WO 00/33078 A1 | 6/2000 |
| WO | WO 2012/147774 A1 | 11/2012 |

OTHER PUBLICATIONS

English translation of Written Opinion of the International Searching Authority, issued in PCT/JP2014/070996, dated Nov. 11, 2014.*
Hilliard et al., "Immobilization of oligonucleotides onto silica nanoparticles for DNA hybridization studies," Anal. Chim. Acta, 2002, vol. 470, issue 1, pp. 51-56.*
Extended European Search Report issued in European Application No. 14836946.5 dated Mar. 15, 2017.
Vejayakumaran et al., "Structural and thermal characterizations of silica nanoparticles grafted with pendant maleimide and epoxide groups," Journal of Colloid and Interface Science, vol. 328, 2008 (available online Sep. 3, 2008), pp. 81-91.
International Search Report, issued in PCT/JP2014/070996, dated Nov. 11, 2014.
Written Opinion of the International Searching Authority, issued in PCT/JP2014/070996, dated Nov. 11, 2014.

* cited by examiner

*Primary Examiner* — Galina M. Yakovleva
(74) *Attorney, Agent, or Firm* — Birch, Stewart, Kolasch & Birch, LLP

(57) ABSTRACT

Silica particles having a thiol group on a surface thereof, and satisfying the following conditions (a) to (c):
(a) a particle diameter is 20 to 1,000 nm;
(b) a density of the thiol group on the surface of the silica particles is 0.002 to 0.2 piece/nm$^2$; and
(c) a ratio (B/A) in terms of an amount B (piece/particle) of the thiol group existing on the surface of the silica particles to an amount A of sulfur elements in the silica particles (the number of sulfur elements derived from thiol per silica particle) is 0.10 to 0.60.

10 Claims, 1 Drawing Sheet

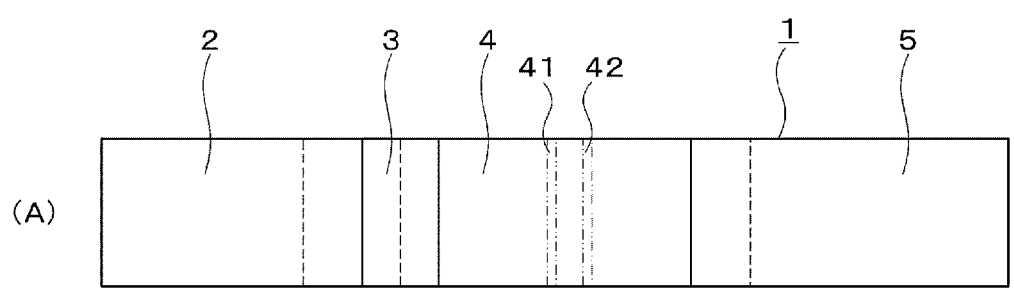
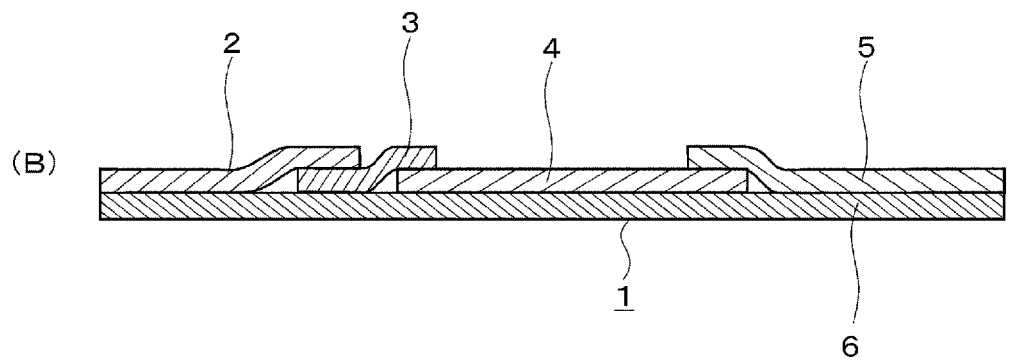

SILICA PARTICLES HAVING REACTIVE FUNCTIONAL GROUP ON SURFACE, AND METHOD OF PRODUCING THE SAME

CROSS-REFERENCE TO RELATED APPLICATIONS

This application is a Continuation of PCT International Application No. PCT/JP2014/070996 filed on Aug. 8, 2014, which claims a priority under 35 U.S.C. § 119 (a) to Japanese Patent Application No. 2013-167902 filed in Japan on Aug. 12, 2013. Each of the above applications is hereby expressly incorporated by reference, in its entirety, into the present application.

TECHNICAL FIELD

The present invention relates to silica particles having a reactive functional group on a surface, and a method of producing the same.

BACKGROUND ART

Fine particles having a diameter of about from several nanometers to 1 μm have been recently applied in various fields and attracted attention. The above-described fine particles include, for example, porous silica particles and zeolite particles to be used for an adsorbent or a catalyst, carbon black, metal oxide particles and inorganic compound particles to be used for a pigment, metal nanoparticles to be used for a conductive material, and silica particles to be used for a reinforcing agent of a resin. Thus, material and use of the fine particles are wide-ranging. Moreover, with regard to semiconductor nanoparticles, silica nanoparticles containing a fluorochrome, and so forth, an application as new labeling particles is expected particularly in a field of biotechnology. In addition, silica nanoparticles containing a dye with high concentration have a high molar extinction coefficient, and thus, an application thereof as further highly sensitive labeling particles is expected.

The above-described labeling particles can be used as a labeling reagent that can be used for detection, quantitative determination, dyeing or the like of a target molecule, by bonding a biomolecule (protein, nucleic acid or the like) having bonding capability with a specific target molecule on the surface of the particles.

Bonding of the labeling particles with the biomolecule is performed by physical adsorption, or also by allowing covalent bonding of both through a reactive functional group existing on the surface of the labeling particles. A stronger and more stable labeled biomolecule can be obtained by utilizing the covalent bond. As a method of introducing the reactive functional group onto the surface of the silica particles, a method is known in which organoalkoxysilane having a reactive functional group on the surface of core particles of silica is subjected to polycondensation in aqueous ammonia-containing solvent (for example, see Patent Literature 1).

CITATION LIST

Patent Literatures

Patent Literature 1: JP-A-2011-225381 ("JP-A" means unexamined published Japanese patent application)

SUMMARY OF INVENTION

Upon introducing a reactive functional group onto the surface of the silica particles, a technique is ordinarily applied in which a silane coupling agent having a functional group and silica particles serving as a core are mixed in acid or basic aqueous solution. Thus, the silane coupling agent is hydrolyzed by moisture in the aqueous solution, and subsequently a polycondensation reaction occurs between the resultant hydrolyzed material and the hydroxyl group on the surface of the silica particles, thereby the reactive functional group being introduced onto the surface of the silica particles. However, it is unavoidable to cause polycondensation in the silane coupling agents having a reactive functional group to each other in this method. Therefore, a shell layer derived from the silane coupling agent having a reactive functional group is formed thick on the surface of the core particles, resulting in a state in which many reactive functional groups are buried in this shell layer. That is, introduction of the reactive functional group onto a surface of the particles has been inefficient in the conventional method.

The present invention is contemplated for providing nanometer sized silica particles having a thiol group with a specific density on a surface, and the silica particles in which a ratio of the thiol group existing on the surface of the particles in a total amount of the thiol group of the particles is improved.

Moreover, the present invention is contemplated for providing biomolecule composite particles formed by bonding of biomolecules through the above-described thiol group on the surface of the above-described silica particles.

Moreover, the present invention is contemplated for providing an immunochromatography method using the biomolecule composite particles on which an antibody or an antigen is bonded as the biomolecule.

Further, the present invention is contemplated for providing a method of producing silica particles onto a surface of which a specific reactive functional group can be further efficiently introduced.

The present inventors found that, when silica particles are dispersed in organic solvent in a state of having bound water on the surface, and a silane coupling agent having a reactive functional group such as a thiol group is mixed into the organic solvent, the reactive functional group can be efficiently introduced onto the surface of the silica particles. That is, the present inventors found that hydrolysis of the above-described silane coupling agent and a polycondensation reaction progress only on the surface of the particles by the above-described bound water, and therefore the polycondensation reaction between the above-described silane coupling agents is hard to occur, and as a result, a thickness of the shell layer having the reactive functional group is significantly suppressed.

Moreover, the present inventors found that the biomolecule is bonded on the surface of the thus obtained silica particles through the reactive functional group, and the resultant material is used as a labeling reagent for immunochromatography or the like, nonspecific adsorption of the labeled reagent is inhibited, a background signal is reduced to give an increased signal/noise ratio, and analysis with higher sensitivity can be conducted.

The present invention has been completed based on these findings.

The problems are solved by the following means.

[1] Silica particles having a thiol group on a surface thereof, and satisfying the following conditions (a) to (c):
(a) a particle diameter is 20 to 1,000 nm;
(b) a density of the thiol group on the surface of the silica particles is 0.002 to 0.2 piece/nm$^2$; and
(c) a ratio (B/A) in terms of an amount B (piece/particle) of the thiol group existing on the surface of the silica particles to an amount A of sulfur elements in the silica particles (the number of sulfur elements derived from thiol per silica particle) is 0.10 to 0.60.

[2] The silica particles described in the above item [1], containing a fluorescence dye or a light absorbing dye.

[3] The silica particles described in the above item [1] or [2], wherein the thiol group is bonded on the surface of the silica particles through an alkylene group or an alkyleneoxy group.

[4] Biomolecule composite particles, wherein a biomolecule is bonded on the surface of the silica particles described in any one of the above items [1] to [3] through the thiol group.

[5] The biomolecule composite particles described in the above item [4], wherein the biomolecule is an antibody or an antigen.

[6] An immunochromatography method, utilizing the biomolecule composite particles described in the above item [5].

[7] A method of producing silica particles having a reactive functional group other than a hydroxy group on a surface thereof, comprising mixing of silica particles having bound water on the surface and a silane coupling agent having a reactive functional group other than a hydroxy group in organic solvent, to hydrolyze the silane coupling agent by the bound water.

[8] The method described in the above item [7], wherein the reactive functional group other than a hydroxy group is at least one selected from the group consisting of a thiol group, an amino group, a carboxy group, a halogen atom, a vinyl group, an epoxy group, an isocyanate group and an isothiocyanate group.

[9] The method described in the above item [7] or [8], wherein the organic solvent is polar aprotic solvent or alcohol having two or more carbon atoms.

[10] The method described in any one of the above items [7] to [9], wherein the silica particles having bound water on the surface contains a fluorescence dye or a light absorbing dye.

[11] The method described in any one of the above items [7] to [10], wherein the silica particles having bound water on the surface are subjected to washing treatment with hydrophilic organic solvent before mixing with the silane coupling agent.

The silica particles of the present invention have the thiol group with the specific density on the surface, and the ratio of the thiol group on the surface of the particles in the total amount of the thiol group of the particles is sufficiently improved.

In the biomolecule composite particles of the present invention, the biomolecule is bonded on the surface of the silica particles of the present invention through the thiol group. Thus, nonspecific adsorption upon being used for an analytical reagent is effectively inhibited and detection sensitivity can be further improved.

In the immunochromatography method according to the present invention, the biomolecule composite particles of the present invention are used as the labeling reagent, and a target substance with which the biomolecule is bonded can be detected with high sensitivity.

According to the production method of the present invention, the specific reactive functional group can be further efficiently introduced onto the surface of the silica particles.

Other and further features and advantages of the invention will appear more fully from the following description, appropriately referring to the accompanying drawing.

BRIEF DESCRIPTION OF DRAWING

FIG. 1 is a drawing schematically showing structure of a test strip used in Example. In FIG. 1, (a) shows a top view and (b) shows a longitudinal sectional view.

MODE FOR CARRYING OUT THE INVENTION

The present invention is described in detail below based on preferred embodiments thereof.

Silica particles of the present invention are silica particles having a particle diameter of 20 to 1,000 nm, and have a thiol group with a specific density on a surface thereof, and a ratio of the thiol group existing on the surface of the particles to a total amount of the thiol group of the particles is improved to a specific level.

Moreover, a production method of the present invention includes mixing of silica particles having bound water on a surface thereof, and a silane coupling agent having a reactive functional group other than a hydroxy group in organic solvent, to hydrolyze the silane coupling agent with the bound water on the surface of the silica particles.

First, a preferred embodiment of the production method according to the present invention is described in detail as follows.

[Production Method of the Present Invention]

(Silica Particles Having Bound Water on Surface)

The silica particles having bound water on the surface (hereinafter, also referred to as "core particles") are not particularly restricted, as long as they have a hydroxy group on the surface and can perform a polycondensation reaction with the silane coupling agent having a reactive functional group described later. When the silica particles are used as a labeling reagent, a labeling substance such as a fluorescence dye or a light absorbing dye, and a radioactive material can be incorporated thereinto. The core particles preferably contain the fluorescence dye or the light absorbing dye, and further preferably contain the fluorescent dye.

A preferred embodiment of the core particles is described as follows.

The core particles having a fluorescence dye or a light absorbing dye can be prepared by obtaining a product (organoalkoxysilane to which the fluorescence dye or light absorbing dye is bonded) in which the dye and a silane coupling agent are bonded by a covalent bond, an ionic bond or any other chemical bond or physical adsorption, and allowing hydrolysis and polycondensation of this product with one kind or two or more kinds of silane compounds (siloxane component), for example, in aqueous ammonia-containing solvent to form a siloxane bond. Moreover, the core particles containing other labeling substances such as the radioactive material without limitation to the dye can be prepared in a similar manner by using a silane coupling agent to which the labeling substance is bonded.

Moreover, when no labeling substance is incorporated into the silica particles, the core particles only need to be obtained by merely allowing hydrolysis and polycondensation of only the above-described silane compound as a raw material in aqueous ammonia-containing solvent.

As the above-described aqueous ammonia-containing solvent, solution prepared by, for example, adding aqueous ammonia having a concentration of about 28%, to be from 0.2 to 3 wt % in an ammonia concentration, to mixed solution in which water/ethanol are adjusted to be from 1/10 to 1/1 in a volume ratio can be used.

The above-described silane compound (siloxane component) is not particularly limited, and for example, a tetraalkoxysilane such as tetraethoxysilane (TEOS) and tetramethoxysilane, can be preferably used. Among those, TEOS can be preferably used.

In the case of allowing covalent bonding of the labeling substance with the silane coupling agent, for example, a labeling substance having an active group such as an N-hydroxysuccinimide (NHS) ester group, a maleimido group, an isocyanate group, an isothiocyanate group, an aldehydo group, a p-nitrophenyl group, a diethoxymethyl group, an epoxy group and a cyano group, and a silane coupling agent having a functional group (for example, an amino group, a hydroxyl group or a thiol group) that can react with these active groups can be used.

Specific preferred examples in the case where the labeling substance having a NHS ester group is a fluorescent molecule include NHS ester group-containing fluorescence dye compounds such as 5-(and -6)-carboxytetramethylrhodamine NHS ester (trade name, manufactured by emp Biotech GmbH), and DY550-NHS ester and DY630-NHS ester (trade name for both, manufactured by Dyomics GmbH) represented by the following formulas. However, the present invention is not limited thereto.

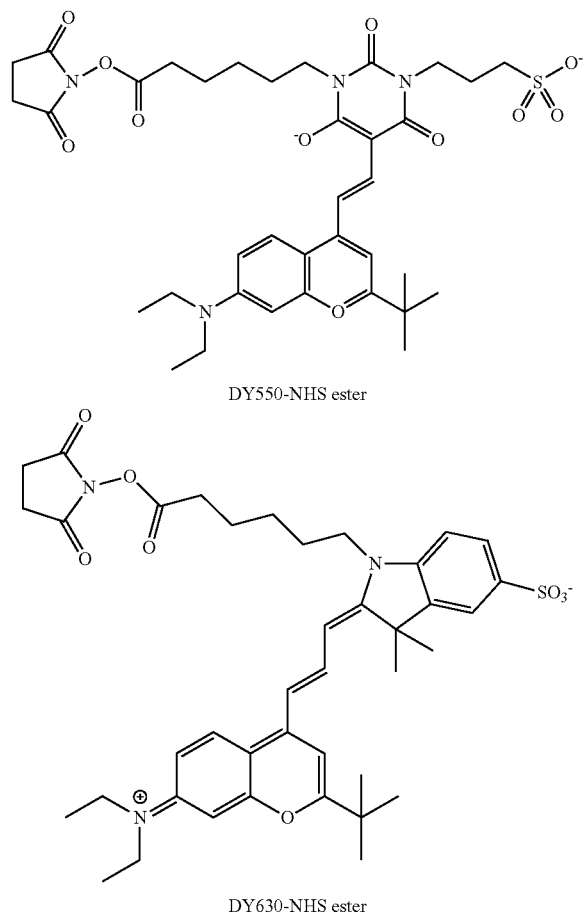

DY550-NHS ester

DY630-NHS ester

When the labeling substance has a succinimide group, the functional molecule can be bonded with a silane coupling agent having an amino group. Examples of the silane coupling agent having an amino group include γ-aminopropyltriethoxysilane (APS), 3-[2-(2-aminoethylamino)ethylamino]propyltriethoxysilane, 3-(2-aminoethylamino)propyldimethoxymethylsilane, and 3-aminopropyltrimethoxysilane. Among them, APS can be preferably used.

A shape of the silica particles containing the labeling substance or containing no labeling substance to be prepared as described above is preferably spherical, in which a ratio of a major axis to a minor axis is preferably 2 or less. Moreover, a mean particle diameter is preferably from 1 to 950 nm, more preferably from 18 to 495 nm, and further preferably from 28 to 298 nm.

The particle diameter herein means the mean particle diameter. The mean particle diameter can be determined, after total occupied areas of particles are determined from projected areas of a total of 50 pieces of particles randomly selected from images of Transmission Electron Microscope (TEM), Scanning Electron Microscope (SEM) or the like by means of an image processor, by calculating as a mean value (mean circle equivalent diameter) of a diameter of a circle equivalent to a value obtained by dividing the above total occupied areas by the number of pieces (50 pieces) of the selected particles. The above-described mean particle diameter includes no particle diameter of secondary particles formed of aggregation of primary particles.

Silica nanoparticles having an intended mean particle diameter can be obtained by ultrafiltration by using an ultrafiltration membrane such as YM-10 and YM-100 (trade names for both, manufactured by Millipore Corporation), or by recovering a supernatant or precipitates after performing centrifugal separation with suitable acceleration of gravity.

The silica particles having bound water on the surface before introducing the reactive functional group other than the hydroxy group thereinto are also preferably washed with water, aqueous solution, organic solvent, or mixed solution thereof. Moreover, removal of impurities and simultaneously retention of sufficient bound water on the surface of the particles can also be made by washing the particles with water or the aqueous solution.

Specifically, a washing operation is preferably performed in 1 to 3 cycles of dispersion of the silica particles into washing liquid, precipitation of the silica particles by centrifugation and removal of a supernatant. The washing liquid is not particularly restricted, and specific examples include water, aqueous solution, ethanol, propanol, pentanol, hexanol, hexanol, N,N-dimethylformamide and dimethylsulfoxide.

The silica particles having bound water on the surface are also preferably obtained by removing the impurities and simultaneously retaining a sufficient amount of bound water on the surface of the silica particles by washing the particles with water or the aqueous solution, and then washing the particles with hydrophilic organic solvent such as alcohol (preferably, ethanol, propanol, pentanol, hexanol or hexanol), and removing excessive moisture (free water) other than the bound water existing on the surface of the silica particles.

Moreover, in the case immediately after the core particles are formed in the aqueous ammonia-containing solvent, sufficient bound water is ordinarily retained on the surface of the core particles. Accordingly, the silica particles having bound water on the surface can be obtained by washing the core particles formed in the aqueous ammonia-containing solvent with the hydrophilic organic solvent, and removing free water existing on the surface of the silica particles.

Subsequently, a method of introducing the reactive functional group (hereinafter, referred to as "functional group (I)") other than the hydroxy group into the silica nanoparticles having bound water on the surface is described. In the production method of the present invention, the functional group (I) is preferably at least one kind selected from the group consisting of a thiol group, an amino group, a carboxy group, a halogen group, a vinyl group, an epoxy group, an isocyanate group and an isothiocyanate group. The biomolecule or the like can be bonded through these reactive functional groups by adopting such a reactive functional group.

(Introduction of Functional Group (I))

The production method of the present invention includes a step of mixing the silica particles having bound water on the surface obtained as described above, and the silane coupling agent having the functional group (I) in the organic solvent to hydrolyze the silane coupling agent by the bound water.

The hydrolyzed silane coupling agent having the functional group (I) as described above is bonded on the surface of the silica nanoparticles by the hydroxy group on a site subjected to hydrolysis and the hydroxy group on the surface of the silica nanoparticles being subjected to polycondensation. A water molecule is released by this polycondensation reaction. Therefore, an amount of bound water does not change before and after the polycondensation reaction.

Examples of the organic solvent include dimethyl sulfoxide, sulfolane, pyridine, N-methylpyrrolidone, N-cyclohexylpyrrolidone, N,N-dimethylformamide, N,N-dimethylacetoamide, and alcohol (preferably that having 2 or more carbon atoms, more preferably having from 3 to 10 carbon atoms, and further preferably having from 4 to 8 carbon atoms). Above all, one selected from N,N-dimethylformamide and alcohol having from 4 to 8 carbon atoms is preferred, and one selected from alcohol having from 4 to 8 carbon atoms is more preferred, and one selected from pentanol, hexanol and heptanol is further preferred.

In the silane coupling agent having the above-described functional group (I), linking of the functional group (I) with a silicon atom is preferably made through a linking group. The linking group is preferably an alkylene group or an alkyleneoxy group. The number of carbon atoms in the alkylene group or the alkyleneoxy group is preferably 2 to 10, more preferably 2 to 5, and further preferably 2 to 4. The functional groups can be effectively arranged toward an outside of the surface of the silica particles due to solvation between the linking group and the organic solvent.

Examples of the silane coupling agent having a functional group (I) include 3-mercaptopropyltrimethoxysilane, γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, 3-[2-(2-aminoethylamino)ethylamino]propyltriethoxysilane, (3-chloropropyltrimethoxysilane, vinylmethoxysilane, 3-methacryloxypropylmethyldimethoxysilane, 3-acryloxypropyltrimethoxysilane, N-phenyl-3-aminopropyltrimethoxysilane, 3-ureidopropyltriethoxysilane, and bis(triethoxysilylpropyl)tetrasulfide, but the present invention is not limited thereto.

The polycondensation reaction between the silane coupling agents having a functional group (I) can be significantly inhibited by introducing the functional group (I) into the silica particles by the above-described method. As a result, the shell layer having the functional group (I) can be further thinned. This thinning of the shell layer causes inhibition of nonspecific adsorption of a component or the like existing in an analyte, upon using the silica particles as labeling particles in an analytical reagent, to allow analysis with excellent sensitivity and accuracy Moreover, because the shell layer can be thinned, a ratio of the core particles can be increased. As a result, an amount of the labeling substance (dye or the like) per particle can be increased, leading to further improvement in sensitivity upon using the particles as the analytical reagent.

The absolute value of zeta (ζ) potential in the functional molecule-containing silica nanoparticles into which the functional group (I) is introduced is preferably from 20 to 70 mV. With regard to the particles in which the absolute value of zeta potential is within the above-described range, aggregation is suppressed and dispersibility is further enhanced.

The zeta potential can be measured using Zetasizer Nano (trade name, manufactured by Malvern Instruments Ltd.), ELS-Z1 (trade name, manufactured by Otsuka Electronics Co., Ltd.) or NICOMP 380ZLS (trade name, manufactured by IBC Advanced Technologies, Inc.) or the like.

According to the production method of the present invention, a ratio of the functional group (I) existing on the surface of the particles in the total amount of the functional group (I) of the silica particles can be improved.

A shape of the silica particles having the functional group (I) on the surface to be prepared as mentioned above is spherical, in which a ratio of a major axis to a minor axis is 2 or less. In practice of the present invention, it is necessary that the silica particles can be centrifuged for solvent replacement required for surface modification. If a particle diameter (mean particle diameter) is smaller than 20 nm, precipitation by centrifugation becomes difficult. Accordingly, the particle diameter is preferably 20 nm or more. Moreover, if the particle diameter is larger than 1,000 nm, the particles are precipitated during reaction. Therefore, the particle diameter is preferably 1,000 nm or less. Thus, the particle diameter is preferably 20 to 1,000 nm, more preferably 20 to 500 nm, and further preferably 30 to 300 nm.

In the production method of the present invention, the functional group (I) is preferably a thiol group. The silica particles obtained when the functional group (I) is the thiol group is described below.

When the functional group (I) is the thiol group, a ratio (B/A) in terms of an amount B of thiol groups existing on the surface of the silica particles (piece/particle) to an amount A of sulfur elements in the silica particles having the thiol group (the number of sulfur elements derived from thiol per silica particle) is preferably 0.10 to 0.60, more preferably 0.15 to 0.60, and further preferably 0.20 to 0.60.

An expression: per piece of particles (per particle) here means a value (namely, a mean value) obtained by dividing the amount of sulfur elements or thiol groups of a predetermined amount of silica particles by the number of particles. Here, the number of silica particles in the predetermined amount can be determined by dividing total mass of the predetermined amount of silica particles by mass per silica particle. The mass per silica particle can be calculated by using a mean volume of the silica particles and specific gravity (2.0 g/cm$^3$) of the silica particles. The mean volume of the silica particles can be calculated by determining particle diameters (means of major axes and minor axes) of individual silica particles of the predetermined number of pieces (ordinarily, about 200 pieces) in a visual field by image processing from a SEM photograph at a magnification of 10,000 times, calculating volumes by using the diameters in assuming that the individual silica particles are spheres (volume=$4\pi\times$(half of particle diameter of silica particles)$^3$/3), determining a total volume based thereon, and dividing the total volume by the prescribed number of pieces (the number of particles) in the above-described visual field.

The above-described ratio (B/A) has the same meaning as a ratio of weight of the sulfur elements exposed on the surface of the silica particles to a total weight of the sulfur elements in the silica particles.

Moreover, when the functional group (I) is the thiol group, a density of the thiol group on the surface of the silica particles is preferably 0.002 to 0.2 piece/nm$^2$, and more preferably 0.002 to 0.1 piece/nm$^2$. Moreover, the density may be 0.002 to 0.05 piece/nm$^2$, 0.003 to 0.02 piece/nm$^2$, or 0.003 to 0.01 piece/nm$^2$.

The biomolecule can be bonded thereto in a sufficient amount by adjusting the density of the thiol group on the surface of the silica particles to 0.002 piece/nm$^2$ or more, and upon application to immunoassay such as immunochromatography, detection sensitivity can be further improved.

Moreover, aggregation of the particles can be effectively inhibited by adjusting the density of the thiol group on the surface of the silica particles to 0.2 piece/nm$^2$ or less. Moreover, upon bonding the biomolecule thereto and using the silica particles as the analytical reagent, the nonspecific adsorption is further inhibited, and false positivity becomes harder to occur.

In addition, in the case where the core particles before introduction of the thiol group onto the surface of the particles have the sulfur element (for example, the sulfur element exists in a portion in which the dye and the silane coupling agent are linked) when the functional group (I) is the thiol group, the amount of sulfur elements in the core particles is not to be included in the amount A of sulfur element in the core particles. That is, the above-described A serves as the total amount of sulfur elements existing in the particles in the form of the thiol group. The core particles before introduction of the thiol group onto the surface of the particles preferably have no sulfur element.

The above-described amount A of sulfur elements in the silica particles having the thiol group on the surface (amount per silica particle having the thiol group) can be measured by a combustion method. Specifically, the amount of sulfur elements can be measured by putting 5 to 50 μg of silica nanoparticles in a metal capsule such as a nickel capsule, and burning the nanoparticles, and quantitatively determining an amount of sulfur dioxide ($SO_2$) produced.

In the above-described silica particles having the thiol group on the surface, the amount B of thiol groups existing on the surface of the particles can be measured using DNTB (5,5'-Dithiobis(2-nitrobenzoic acid) as a reagent. The quantitative determination method of the thiol group using DNTB, is described in, for example, Archives of Biochemistry and Biophysics, 1959, vol. 82, p. 70. As one example of a specific method, 20 μL of solution of 10 mM DNTB dissolved in a phosphate buffer (pH 7.0), and 2.5 mL of silica nanoparticle colloid prepared in 200 mg/mL, are mixed, and after 1 hour, absorbance at 412 nm is measured, and then the thiol group can be quantitatively determined from a calibration curve prepared using γ-mercaptopropyltrimethoxysilane (MPS) as a reference material.

The silica particles having the thiol group on the surface to be obtained by the production method according to the present invention can bond the biomolecule through the thiol group, and can be formed into biomolecule composite particles. Bonding of the biomolecule is described later.

Moreover, in the production method of the present invention, when the functional group (I) of the silica particles is the amino group, the carboxy group, the vinyl group, the epoxy group, the isocyanate group or the isothiocyanate group, the biomolecule can be bonded on the surface of the resultant silica particles by the conventional method. For these methods, descriptions in JP-A-2009-274923 (amino group), JP-A-2009-162537 (carboxy group) or JP-A-2010-100542 (epoxy group or isocyanate group) can be referred to, for example.

[Silica Particles of the Present Invention]

The silica particles of the present invention have the thiol group on the surface, in which (a) a particle diameter is 20 to 1,000 nm, (b) a density of the thiol group on the surface of the particles is 0.002 to 0.2 piece/nm$^2$, and further (c) a ratio (B/A) in terms of the amount B (piece per particle) of thiol groups existing on the surface of the silica particle to the amount A of a sulfur element in the silica particles (the number of sulfur elements derived from thiol per silica particle) is 0.01 to 0.60. In the silica particles of the present invention, the thiol groups ordinarily uniformly exist on the surface.

A method of producing the silica particles according to the present invention is not particularly restricted. For example, the silica particles can be obtained by adopting the thiol group as the functional group (I) in the above-described production method.

A preferred aspect of the silica particles according to the present invention is the same as the preferred embodiment of the silica particles obtained when the thiol group is adopted as the functional group (I). Accordingly, a particle diameter of the silica particles according to the present invention is preferably 20 to 500 nm, and more preferably 30 to 300 nm. A density of the thiol group on the surface of the silica particles is preferably 0.002 to 0.1 piece/nm$^2$, and may be 0.002 to 0.05 piece/nm$^2$, or 0.003 to 0.002 piece/nm$^2$. With regard to the silica particles of the present invention, the above-described ratio (B/A) is preferably 0.15 to 0.60, and more preferably 0.20 to 0.60.

The silica particles of the present invention need not to contain the labeling substance, but preferably contains the labeling substance. The silica particles can be preferably used as the labeling reagent by containing the labeling substance. The labeling substance is preferably a fluorescence dye or a light absorbing dye, and more preferably a fluorescence dye. The dye is preferably incorporated into the particles (core particles) before introduction of the thiol group. That is, the silica particles in the form of containing the labeling substance according to the present invention can be obtained by preparing the core particle containing the labeling substance, and introducing the thiol group onto the surface, for example, by the production method according to the present invention. Preparation of the core particles is as mentioned above. In the above-described core particles, no sulfur element is preferably contained.

[Biomolecule Composite Particles of the Present Invention]

The biomolecule composite particles of the present invention are particles in the form in which the above-described silica particles according to the present invention bond the biomolecule through the thiol group having on the surface.

The biomolecule is not particularly restricted, and a protein, a nucleic acid, a saccharine or the like can be broadly used. These biomolecules may be further chemically modified, and a part of a structure thereof may be chemically modified. Above all, the biomolecule preferably has a specific bonding capability with a desired target substance. Specific examples of combinations of the biomolecule and the target substance include an antibody and an antigen thereof, an antigen and an antibody thereof, nucleic acid (DNA, RNA or the like) and nucleic acid having a complementary sequence to the nucleic acid, a receptor and a ligand thereof, a ligand and a receptor thereof, lectin and a glycan, and an aptamer and a molecule to be specifically bonded with the aptamer. The biomolecule is preferably an antibody or an antigen, and more preferably an antibody.

When the above-described biomolecule is the antibody, the biomolecule composite particles of the present invention can be used as an immunoassay reagent for detecting the antigen.

Examples of the above-described antibody includes immunoglobulin (whole antibody), F(ab')$_2$ or Fab obtained by performing enzymolysis thereof, scFv or sc(Fv)$_2$ in which a heavy chain variable region (VH) and a light chain variable region (VL) are linked in tandem through a linker, a diabody formed of 2 units in which VH and VL are linked through a linker, an artificially chemically synthesized polyamino acid containing VH and VL, and a recombinant protein or recombinant polyamino acid containing VH and VL produced by using *Escherichia coli*, yeast or the like as an expression system. More specifically, "antibody" in the present invention means a molecule or unit having VH and VL, and a structure thereof is not limited, as long as the antibody has VH and VL.

Bonding of the biomolecule to the silica particles according to the present invention is preferably performed by allowing covalent bonding of the thiol group existing on the surface of the particles to the biomolecule. The covalent bonding can be performed by a conventional method. For example, the silica particles of the present invention and a linker molecule having a maleimide group and a carboxy group are allowed to coexist in aprotic solvent to form a thioether bond between the thiol group on the surface of the particles and the above-described maleimide group, to obtain the silica particles bonded with the linker molecule. Subsequently, the silica particles bonded with the above-described linker molecule, carbodiimide, and a biomolecule having an amino group are allowed to coexist in aqueous solvent to form an amide bond between the above-described carboxy group subjected to active esterification by the above-described carbodiimide, and the amino group of the above-described biomolecule. Thus, the biomolecule composite particles formed by bonding the biomolecule through the thiol group can be obtained.

Moreover, the silica particles having the thiol group on the surface and the linker molecule having the maleimide group and the amino group may be allowed to coexist in solvent to form the thioether bond between the thiol group of the silica particles having the thiol group, and the above-described maleimide group, and then to obtain the silica particles bonded with the linker molecule. Subsequently, the silica particles bonded with the above-described linker molecule, carbodiimide, and the antibody may be allowed to coexist in aqueous solvent to form the amide bond between the amino group of the above-described linker molecule, and the carboxy group of the above-described antibody.

In the biomolecule composite particles produced by the production method according to the present invention, a particle diameter (mean particle diameter) is preferably 20 to 1,000 nm, more preferably 20 to 500 nm, and further preferably 30 to 300 nm.

An application of the biomolecule composite particles according to the present invention is not particularly restricted. For example, when the antibody or antigen is used as the biomolecule, the biomolecule composite particles can be used as the labeling reagents for various immunological testing (immunoassay). In the immunoassay, the biomolecule composite particles can be applied as the labeling particles for immunochromatography, enzyme immunoassay (EIA, for example, Enzyme-Linked Immunosorbent Assay (ELISA)), fluorescent immunoassay (FIA), radioimmunoassay (RIA) or the like.

Moreover, the biomolecule composite particles can also be utilized in immunoagglutination assay (testing method in which particles bonded with an antibody or antigen, and an analyte are mixed to aggregate the particles by an antigen-antibody reaction with the antigen or antibody contained in the analyte), immunoturbidimetry (testing method in which the particles bonded with the antibody or antigen, and the analyte are mixed to form precipitates of an antigen-antibody composite to be produced by the antigen-antibody reaction with the antigen or antibody contained in the analyte, the aggregate is irradiated with light, and attenuation of irradiated light by scattering is measured by a spectrophotometer to measure the amount of the antigen contained in the analyte), immunonephelometry (testing method in which the particles bonded with the antibody or antigen, and the analyte are mixed to form an antigen-antibody complex to be produced by the antigen-antibody reaction with the antigen or antibody contained in the analyte, dispersion liquid of the complex is irradiated with light, and scattered light is measured to quantitatively determine the antigen or antibody contained in the analyte), a CLEIA method (chemiluminescent enzyme immunoassay; testing method in which the particles bonded with the antigen, and an analyte containing an enzyme-labeled antibody and an antigen are mixed to form a composite of particles-antigen-enzyme-labeled antibody, an unreacted matter is removed, and then a light-emitting reagent is added thereto, and the light emitting amount is measured to quantitatively determine a detecting object), or the like.

In addition thereto, the biomolecule composite particles of the present invention can be utilized as the labeling particles in flow cytometry, the labeling particles in various biochips or the like.

[Immunochromatography Method According to the Present Invention]

A preferred embodiment of the immunochromatography method (immunochromatography) according to the present invention is described.

(Test Strip)

The immunochromatography method of the present invention is performed using a specific test strip. The test strip preferably has a structure, in which:

(1) a member for adding a sample (sample pad), and a member (conjugate pad) formed by incorporating a labeled antibody (silica particles being biomolecule composite particles containing a fluorescence dye or a light absorbing dye, and the biomolecule being an antibody);

(2) the above-described conjugate pad, and a membrane (captured antibody-immobilized membrane) immobilized with an antibody for capturing a composite containing a target substance and a labeled antibody; and (3) the above-described captured antibody-immobilized membrane, and an absorbent pad;

are preferably linked in series such that the capillary phenomenon may occur to each other.

The above-described captured-antibody molecule is an antibody that can bond to a moiety other than the moiety bonded with the labeled antibody on the target substance in the composite containing the target substance and the labeled antibody.

A preferred embodiment of the above-described test strip is described, referring to FIGS. 1(A) and 1(B), but the present invention is not restricted thereto.

FIG. 1(A) is a plan view showing one preferred embodiment of the above-described test strip, and FIG. 1(B) is a diagram showing a longitudinal cross-sectional view of the test strip shown in FIG. 1(A).

The above-described test strip 1 is preferably formed of a sample pad 2, a conjugate pad 3, a captured antibody-immobilized membrane 4 and an absorbent pad 5. Each of the above-described constitutional members is preferably lined by a backing sheet 6 added with an adhesive.

A determination part 41 immobilized with an antibody for determining existence or non-existence of the target substance, namely for determining positive/negative is provided for the captured antibody-immobilizing part in the above-described captured antibody-immobilized membrane 4. The captured antibody-immobilized membrane 4 preferably contains a control line 42 immobilized with a molecule to be bonded with the labeled antibody.

Next, each of the above-described members is described below.

(Sample Pad 2)

The sample pad 2 is a constitutional member to which a liquid sample containing a target substance is loaded.

(Conjugate Pad 3)

The conjugate pad 3 is a constitutional member containing the labeled antibody, and a part from which formation of a complex is started, in which the target substance contained in the liquid sample moved from the sample pad 2 due to the capillary phenomenon is bonded with the labeled antibody by a specific molecular-recognized reaction in a liquid phase.

(Antibody-Immobilized Membrane 4)

The captured antibody-immobilized membrane 4 is a constitutional member in which solution containing the above-described complex is moved due to the capillary phenomenon, and has a captured antibody-immobilizing part (determination parts) in which the complex containing the target substance and the labeled antibody are captured on the immobilized antibody.

The shape of the captured antibody-immobilizing part (determination part) in the membrane is not particularly limited as long as an immobilized antibody is locally immobilized, and examples thereof include a line shape, a circular shape, a band shape, or the like. Among these, the line shape is preferable, and the line shape with width of from 0.5 to 1.5 mm is usual.

The labeled antibody is resulted in being concentrated in the captured antibody-immobilizing part (determination part) by the above-described complex forming reaction. As a result, an amount of the target substance can be qualitatively or quantitatively determined depending on a degree of the amount of dye of the dye-containing silica particles, such as a fluorescent signal.

Although the captured antibody immobilization amount in each of the captured antibody-immobilizing part (determination part) is not particularly limited, when it has a line shape, it is preferably from 0.1 μg to 5 μg per unit length (cm). Examples of the immobilization method include a method of coating, applying or spraying captured antibody solution, drying it, and immobilizing the antibody by physical adsorption. The captured-molecule may be directly immobilized to the membrane or may be indirectly immobilized thereto through other molecules.

To avoid an influence of non-specific adsorption on measurement after captured antibody immobilization described above, the entire captured-antibody-immobilized membrane is preferably subjected to so-called blocking treatment in advance. For example, the blocking treatment is conducted by impregnating in buffer solution containing a blocking agent such as albumin, casein, and polyvinyl alcohol for an appropriate time followed by drying. Examples of a commercially available blocking agent include skim milk (manufactured by DIFCO) and 4% Block Ace (manufactured by Meiji Dairies Corporation).

(Absorbent Pad 5)

The absorption pad 5 is a constitutional membrane for absorbing solution which migrates along the membrane based on capillary phenomenon, and generating a constant flow of them at all times.

The material of each of the aforementioned constitutional members is not particularly limited. Instead, members used for a test strip for immunochromatography can be used. Preferred examples of the sample pad and the conjugate pad include a pad of glass fiber such as Glass Fiber Conjugate Pad (trade name, manufactured by MILLIPORE). Preferred examples of the membrane include a nitrocellulose membrane such as Hi-Flow Plus120 (trade name, manufactured by MILLIPORE). Further, preferred examples of the absorption pad include a cellulose membrane such as Cellulose Fiber Sample Pad (trade name, manufactured by MILLIPORE).

Examples of the backing sheet added with adhesives include AR9020 (trade name, manufactured by Adhesives Research).

With regard to a method for producing the test strip, a sample pad, a conjugate pad, a captured-antibody-immobilized membrane, and an absorption pad are overlaid in that order while both ends of each member are attached to the neighboring member such that they are overlapped with each other within a range of 1 to 5 mm (preferably, on a backing sheet) so as to easily cause capillary phenomenon between the respective members.

(Detection Method)

Next, the detection method according to the immunochromatography is described below.

The liquid sample that may contain the target substance is added dropwise to the sample pad 2 of the above-described test strip. Thus, the liquid sample passed through the sample pad 2 is permeated into the conjugate pad 3 and brought into contact therewith, and a bonding reaction starts between the labeled antibody retained in the conjugate pad 3, and the target substance in the liquid sample. While the liquid sample forms a complex containing the labeled antibody and the target substance by the above-described bonding reaction, the liquid sample sequentially moves to the captured antibody-immobilized membrane 4 and the absorption pad 5 due to the capillary phenomenon. When the target substance is contained in the sample, the labeled antibody is concentrated on the test line as mentioned above. Existence of the target substance can be detected by visually observing absorption of light (Plasmon resonance) of the dye contained in this concentrated labeled antibody, or by detecting fluorescence of the dye by using a fluorescence detector. "Detection" in the present invention has a concept including both qualitative detection and quantitative detection.

An amount of the liquid sample to be added dropwise thereto can be appropriately adjusted according to the constitution of the test strip.

In the present invention, the sample that may contain the target substance is not particularly restricted, and examples include a clinical analyte, a food analyte and an environmental sampling analyte.

Specific examples of the above-described clinical analyte include body fluid or feces, such as blood, plasma, serum, lymph fluid, urine, saliva, pancreatic fluid, stomach fluid, sputum, and swab collected from a mucous membrane of a nose or throat, but are not limited thereto. The analyte only needs to be a sample in which an objective target substance may be contained.

Specific examples of the above-described food analyte include liquid beverage, semi-solid food and solid food.

Specific examples of the environmental sampling analyte include a sample in natural such as soil, river and sea water, and also a sampling analyte by an air sampler installed in a production line or a clean room in a plant, and an analyte obtained by wiping thereof.

When the sample is liquid, it can be used as it is in the method according to the present invention. When the sample is semi-solid, solid or the like, it can also be used in the present invention after it undergoes treatment such as dilution or extraction.

The immunochromatography method of the present invention is preferably carried out under a temperature of 5 to 40° C.

When the biomolecule composite particles of the present invention are used as the labeled antibody in the immunochromatography, the nonspecific adsorption of a component other than the target substance existing in the analyte onto the labeled antibody is hard to occur. As a result, an analysis with higher sensitivity and higher accuracy can be conducted.

EXAMPLES

[Example 1] Preparation of Dye-Containing Silica Particles Having Reactive Functional Group on Surface Dye-containing silica particles having a thiol group as a reactive functional group on a surface thereof were prepared through the following steps (i) to (iv).

—Step (i): Preparation of Core Particles—

First, 3.5 mL of aqueous ammonia-containing organic solvent was prepared by diluting 14% aqueous ammonia with ethanol by 5 times. Into this aqueous ammonia-containing organic solvent, 0.86 vol % of TEOS based on 100 vol % of the aqueous ammonia-containing organic solvent, and 53 vol % of DMF solution of carboxyrhodamine 6G-APS based on 100 vol % of the TEOS were added, respectively, and the resultant mixture was stirred under a temperature of 40° C. Here, this carboxyrhodamine 6G-APS is a product obtained by allowing carboxyrhodamine 6G-NHS ester to react with APS. Moreover, a concentration of carboxyrhodamine 6G-APS in the above-described DMF solution was adjusted to 10 mM.

—Step (ii): Formation of Shell Layer—

To the dispersion liquid of the dye-containing silica particles formed in the above-described step (i), the above-described carboxyrhodamine 6G-APS and TEOS were further added, and allowed to react at 40° C. for 30 minutes to form a shell layer.

The addition amount of the above-described carboxyrhodamine 6G-APS was adjusted to 67 vol % based on 100 vol % of the addition amount of carboxyrhodamine 6G-APS in the above-described step (i), and the addition amount of TEOS was adjusted to the same amount with the addition amount of TEOS in the above described step (i).

Dye-containing silica particles having a two-layered shell layer were prepared by repeating this operation to laminate the shell layers. The second-time addition amount of carboxyrhodamine 6G-APS was adjusted to 33 vol % based on 100 vol % of the addition amount of carboxyrhodamine 6G-APS in the above-described step (i), and the second-time addition amount of TEOS was also adjusted to 33 vol % based on 100 vol % of the addition amount of TEOS in the above-described step (i).

—Step (iii): Removal of Free Water—

The dispersion liquid of the dye-containing silica particles having the two-layered shell layer obtained in the above-described step (ii) was subjected to centrifugation (10,000 rpm, 10 minutes) to precipitate the particles, and then a supernatant was immediately removed. The obtained precipitates were re-dispersed in ethanol and again subjected to centrifugation (10,000 rpm, 10 minutes) to precipitate the particles and the supernatant was removed.

—Step (iv): Introduction of Reactive Functional Group—

The dye-containing silica particles having bound water on the surface obtained in the above-described step (iii) were re-dispersed in 3.5 mL of each of various solvents shown in Table 1 (Conditions 1 to 5.) Here, Condition 1 was in Comparative Example, and Conditions 2 to 5 were in examples of the present invention. Next, 3-mercaptopropyltrimethoxysilane (MPMS) was charged into dispersion liquid of the particles in order to introduce a thiol group into a surface layer of the particles, and the resultant mixture was allowed to react at 40° C. for 20 minutes to obtain silica nanoparticles having a hydroxy group and a thiol group in the surface layer. The charge amount of MPMS was adjusted to 33 vol % based on 100 vol % of the total charge amount of TEOS and carboxyrhodamine 6G-APS in the above-described step (i) with regard to Conditions 1 to 4, and was adjusted to 10 vol % based on 100 vol % of the total charge amount of TEOS and carboxyrhodamine 6G-APS in the above-described step (i) with regard to Condition 5.

TABLE 1

| | Solvent |
|---|---|
| Condition 1 | Water + Ammonia water + Ethanol (Same solvent as step (a)) |
| Condition 2 | Ethanol |
| Condition 3 | Hexanol |
| Condition 4 | N,N-dimethylformamide |
| Condition 5 | Hexanol |

After the reaction was completed, particles were precipitated by performing centrifugation (10,000 rpm, 10 minutes), and the supernatant was immediately removed. The obtained precipitates were re-dispersed in ethanol and again subjected to centrifugation (10,000 rpm, 10 minutes) to precipitate the particles. A similar washing operation with ethanol was further performed once, and unreacted TEOS or the like was removed. Subsequently, the washing operation was performed 4 times in a similar manner as described above to remove a free dye or the like except that distilled water was used in place of ethanol. Thus, five kinds of thiol group-introduced dye-containing silica particles in which reaction solvents were different were obtained.

(Measurement of Zeta (ζ) Potential and Quantitative Determination of Thiol Group)

The thiol group-introduced dye-containing silica particles obtained as described above were washed, and measurement was performed on a mean particle diameter, ζ-potentiometry, an amount of sulfur element (amount of sulfur contained in the particles) by a combustion method, and quantitative determination of a thiol group by DNTB was performed.

The thus obtained results are shown in Table 2 below.

TABLE 2

| Condition | Average particle diameter | ζ-potential | The number of sulfur elements in particle (A) (per particle) | The number of thiol groups as reactive group on particle surface (B) (DNTB) (per particle) | B/A |
|---|---|---|---|---|---|
| 1 | 310 nm | −58 mV | 6.1 × 10$^6$ pieces | 1,000 pieces | 0.0002 |
| 2 | 300 nm | −58 mV | 1.0 × 10$^4$ pieces | 1,500 pieces | 0.15 |
| 3 | 300 nm | −53 mV | 1.0 × 10$^4$ pieces | 2,000 pieces | 0.20 |
| 4 | 300 nm | −50 mV | 1.0 × 10$^4$ pieces | 1,500 pieces | 0.15 |
| 5 | 300 nm | −50 mV | 3.3 × 10$^3$ pieces | 2,000 pieces | 0.60 |

The density of the thiol group on the surface of the thiol group-introduced dye-containing silica particles obtained under Conditions 1 to 5 was 0.0033 piece/nm$^2$, 0.0053 piece/nm$^2$, 0.0071 piece/nm$^2$, 0.0053 piece/nm$^2$ and 0.0071 piece/nm$^2$ in this order.

As shown in Table 2, B/A was significantly improved in the thiol group-introduced dye-containing silica particles prepared in the examples of the present invention (Conditions 2 to 5). That is, the shell layers formed by MPMS being subjected to polycondensation were markedly thinner in the thiol group-introduced dye-containing silica particles prepared in the examples of the present invention, in comparison with the shell layer formed by MPMS being subjected to polycondensation in the thiol group-introduced dye-containing silica particles prepared in Comparative Example (Condition 1).

This result shows that the thiol group can be significantly efficiently introduced onto the surface of the particles by allowing polycondensation of the silane coupling agent having the reactive functional group onto the surface of the particles in the organic solvent.

[Example 2] Introduction of Antibody to Thiol Group-Introduced Dye-Containing Silica Particles To 40 μL of dispersion liquid (concentration: 25 mg/mL, dispersion medium: distilled water) of the thiol group-introduced dye-containing silica particles obtained in the step (iv), 460 μL of DMF was added, and the resultant mixture was centrifuged at a gravitational acceleration of 15,000×g for 10 minutes. A supernatant was removed, and 500 μL of DMF was added thereto, and the resultant mixture was centrifuged, and a supernatant was removed. Then, 500 μL of DMF was again added thereto to disperse thiol group-introduced fluorescent silica nanoparticles therein. As a linker molecule, 1 mg of 3-maleimide benzoic acid was added thereto, and the resultant mixture was mixed for 30 minutes to form a thioether bond between a maleimide group of the above-described linker molecule and a thiol group of the thiol group-introduced dye-containing silica particles.

This reaction mixture was centrifuged at gravitational acceleration of 15,000×g for 10 minutes, a supernatant was removed, and then 90.6 μL of distilled water was added to disperse particles. Subsequently, 100 μL of 0.5 M MES (2-morpholinoethane sulfonic acid) (pH 6.0), 230.4 μL of 50 mg/mL NHS (N-hydroxysuccinimide), 75 μL of 19.2 mg/mL EDC (1-ethyl-3-(3-dimethylaminopropyl)carbodiimide) were added thereto, and the resultant mixture was mixed. There, 4.0 μL of anti-influenza A nucleoprotein antibody (6.2 mg/mL, manufactured by HyTest, Ltd.) was added, and the resultant mixture was mixed for 10 minutes.

The reaction solution was centrifuged at a gravitational acceleration of 15,000×g for 10 minutes, and the supernatant was removed. There, 400 μL of 10 mM KH$_2$PO$_4$ (pH 7.5) was added to disperse particles. Subsequently, the reaction solution was centrifuged at a gravitational acceleration of 15,000×g for 10 minutes, and the supernatant was removed. Then, 400 μL of 10 mM KH$_2$PO$_4$ (pH 7.5) was again added to disperse particles, and thus colloid was obtained.

Subsequently, 10 μL of 10% BSA was added to the above-described colloid, and the resultant mixture was mixed for 10 minutes. The reaction solution was centrifuged at a gravitational acceleration of 15,000×g for 10 minutes, and the supernatant was removed. Then, 500 μL of 10 mM KH$_2$PO$_4$ (pH 7.5) was added to disperse particles, the resultant mixture was centrifuged at a gravitational acceleration of 15,000×g for 10 minutes, and a supernatant was removed. Then, 400 μL of 10 mM KH$_2$PO$_4$ (pH 7.5) was again added to disperse particles, and thus colloid in which dye-containing silica particles (biomolecule composite particles) on which the anti-influenza A nucleoprotein antibody was bonded were dispersed was obtained.

[Test Example 1] Immunochromatography Test (Rapid Judgment of Influenza Nucleoprotein)

(Preparation of Test Strip for Immunochromatography)
A test strip using an antibody-immobilized membrane was prepared by the following method.

At a position of about 6 mm from an end of a membrane (length: 25 mm, trade name: Hi-Flow Plus120 Membrane, manufactured by Millipore Corporation), solution ((50 mM KH$_2$PO$_4$, pH 7.0)+5% sucrose) containing 1 mg/mL of rabbit-derived anti-influenza A nucleoprotein antibody (polyclonal antibody, manufactured by our company) was applied in an application amount of 0.75 μL/cm, to provide a test line having a width of about 1 mm for influenza A.

Subsequently, solution ((50 mM KH$_2$PO$_4$, pH 7.0), sugar-free) containing 1 mg/mL of goat-derived anti-mouse IgG antibody (AKP Goat anti-mouse IgG Antibody, manufactured by BioLegend, Inc.) was applied in an application amount of 0.75 μL/cm, to provide a control line having a width of about 1 mm. Then, the resultant material was dried at 50° C. for 30 minutes. Herein, the interval between the test line and the control line was adjusted to 3 mm.

The above-described antibody-immobilized membrane, a sample pad (Glass Fiber Conjugate Pad (GFCP), manufactured by Millipore Corporation), and an absorbent pad (Cellulose Fiber Sample Pad (CFSP), manufactured by Millipore Corporation) were assembled on a backing sheet (trade name AR9020, manufactured by Adhesives Research, Inc.). The membranes were provided such that the test line for influenza A was directed to a side of the sample pad and the control line was directed to a side of the absorbent pad.
(Detector)
A detector which had a detection unit composed of a light source, an optical filter and a photomultiplier tube (PMT) was prepared. The detection unit could linearly move at a constant speed by a motor. The detector was equipped with a recording mechanism of light-receiving intensity of PMT, and the recording was performed every 50 μseconds. The light source was a laser diode having a wavelength of 532 nm. A sample is irradiated with light from the laser diode and reflected light thorough an optical filter transmittable for only light having a wavelength of 550 nm or more was received in the photomultiplier tube (PMT).

(Immunochromatography Test)

Solution of influenza A nucleoprotein having a concentration shown in Table 3 was prepared. Mixed fluid of 100 μL of this solution and 2 μL of colloid (2.5 mg/mL) in which the dye-containing silica particles bonded with the above-described anti-influenza A nucleoprotein antibody were dispersed was added dropwise onto the sample pad part of the test strip. After 15 minutes, visual observation was carried out. Moreover, fluorescence intensity of the test line as measured by the above-described detector was converted into numeral values. The results are shown in Tables 3 and 4.

Tables 3 and 4 describe the solvents used for introducing thiol thereinto for each of the thiol group-introduced dye-containing silica particles that were used for preparation of the dye-containing silica particles bonded with the anti-influenza A nucleoprotein antibody. Moreover, in Table 3, "−" means being undetectable, and "+" means being detectable.

TABLE 3

The results of visual observation

| Influenza A nucleo-protein (ng/mL) | Condition 1 (Water + Ammonia water + Ethanol) | Condition 2 (Ethanol) | Condition 3 (Hexanol) | Condition 4 (N,N-dimethyl-formamide) | Condition 5 (Hexanol) |
|---|---|---|---|---|---|
| 0 | − | − | − | − | − |
| 20 | − | − | + | − | + |
| 30 | − | + | + | + | + |
| 50 | + | + | + | + | + |

TABLE 4

The results of measuring fluorescence intensity of the test line with a detector Fluorescence intensity of test line (a.u.)

| Influenza A nucleo-protein (ng/mL) | Condition 1 (Water + Ammonia water + Ethanol) | Condition 2 (Ethanol) | Condition 3 (Hexanol) | Condition 4 (N,N-dimethyl-formamide) | Condition 5 (Hexanol) |
|---|---|---|---|---|---|
| 0 | 0 | 0 | 0 | 0 | 0 |
| 20 | 30 | 35 | 50 | 30 | 70 |
| 30 | 40 | 65 | 80 | 60 | 90 |
| 50 | 145 | 160 | 250 | 210 | 280 |

In comparison with the case where the silica particles obtained by introducing the thiol group thereinto in the water-containing solvent were used (Condition 1), detection sensitivity by visual observation was improved (Table 3), in the cases where the silica particles obtained by introducing the thiol group thereinto in the organic solvent were used (Conditions 2 to 5), and also in fluorescence detection, the fluorescence intensity was higher to give superb detection sensitivity (Table 4).

Table 4 shows fluorescence intensity when fluorescence intensity at 0 ng/mL in the influenza A nucleoprotein was taken as 0. Although not shown in Table 4, when the dye-containing silica particles bonded with the anti-influenza A nucleoprotein antibody that were prepared by using the thiol group-introduced dye-containing silica particles in the comparative example were used (Condition 1), the fluorescence intensity (background signal) when the influenza A nucleoprotein was 0 ng/mL was higher in comparison with the cases where the dye-containing silica particles bonded with the anti-influenza A nucleoprotein antibody that were prepared by using the thiol group-introduced dye-containing silica particles were used in the examples of the present invention (Conditions 2 to 5).

The results in Tables 3 and 4 show that, when the dye-containing silica particles bonded with the anti-influenza A nucleoprotein antibody that were prepared by using the thiol group-introduced dye-containing silica particles in the example of the present invention were used, the signal/noise ratio (S/N ratio) was larger to give superb detection sensitivity.

The reasons why such superb detection sensitivity was obtained when the thiol group-introduced dye-containing silica particles in the examples of the present invention were used are considered such that; 1) the shell layer of MPMS was thin (Table 2) in the thiol group-introduced dye-containing silica particles that were prepared in the examples of the present invention, the nonspecific adsorption of the biomolecule composite particles obtained therefrom was inhibited, and the background signal was reduced; and also 2) the introduced thiol groups were arranged toward an outside of the particles due to a thiol group solvation effect, and the antibody bonded with the thiol group was facilitated to be bonded with the antigen. In particular, when the silica particles obtained by introducing the thiol group thereinto in hexanol having high hydrophobicity were used (Conditions 3 and 5), B/A could be further improved, and improvement of the detection sensitivity was further significant.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Test strip
2 Sample pad
3 Conjugate pad
4 Antibody-immobilized membrane
41 Determination part (Test line)
42 Control line
5 Absorbent pad
6 Backing sheet

The invention claimed is:

1. Silica particles having a thiol group on a surface thereof, and satisfying the following conditions (a) to (c):
   (a) a particle diameter is 20 to 1,000 nm;
   (b) a density of the thiol group on the surface of the silica particles is 0.002 to 0.2 piece/nm$^2$; and
   (c) a ratio (B/A) in terms of an amount B (piece/particle) of the thiol group existing on the surface of the silica particles to an amount A of sulfur elements in the silica particles (the number of sulfur elements derived from thiol per silica particle) is 0.10 to 0.60,
   wherein the silica particles having a thiol group on a surface thereof are produced by a method comprising:
   forming silica particles having bound water on the surface by allowing hydrolysis and polycondensation of one kind or two or more kinds of silane compounds in an aqueous ammonia-containing solvent to form a siloxane bond;
   washing the silica particles having bound water on the surface with a hydrophilic organic solvent to remove free water other than the bound water existing on the surface of the silica particles; and mixing the silica particles having bound water on the surface and a silane coupling agent having a reactive functional group including a thiol group; in an organic solvent to hydrolyze the silane coupling agent by the bound water existing on the surface of the silica particles.

2. The silica particles according to claim 1, comprising a fluorescence dye or a light absorbing dye.

3. The silica particles according to claim 1, wherein the thiol group is bonded on the surface of the silica particles through an alkylene group or an alkyleneoxy group.

4. Biomolecule composite particles, wherein a biomolecule is bonded on the surface of the silica particles according to claim 1 through the thiol group.

5. The biomolecule composite particles according to claim 4, wherein the biomolecule is an antibody or an antigen.

6. An immunochromatography method, utilizing the biomolecule composite particles according to claim 5.

7. A method of producing silica particles of claim 1, the method comprising:

forming silica particles having bound water on the surface by allowing hydrolysis and polycondensation of one kind or two or more kinds of silane compounds in an aqueous ammonia-containing solvent to form a siloxane bond;

washing the silica particles having bound water on the surface with a hydrophilic organic solvent to remove free water other than the bound water existing on the surface of the silica particles; and mixing the silica particles having bound water on the surface and a silane coupling agent having a reactive functional group including a thiol group; in an organic solvent to hydrolyze the silane coupling agent by the bound water existing on the surface of the silica particles.

8. The method according to claim 7, wherein the organic solvent is polar aprotic solvent or alcohol having two or more carbon atoms.

9. The method according to claim 7, wherein the silica particles having bound water on the surface comprises a fluorescence dye or a light absorbing dye.

10. Silica particles having a thiol group on a surface thereof, and satisfying the following conditions (a) to (c):

(a) a particle diameter is 20 to 1,000 nm;

(b) a density of the thiol group on the surface of the silica particles is 0.002 to 0.2 piece/nm$^2$; and (c) a ratio (B/A) in terms of an amount B (piece/particle) of the thiol group existing on the surface of the silica particles to an amount A of sulfur elements in the silica particles (the number of sulfur elements derived from thiol per silica particle) is 0.10 to 0.60, said silica particles further comprising a fluorescence dye or a light absorbing dye, wherein the thiol group is bonded on the surface of the silica particles through an alkylene group or an alkyleneoxy group, wherein a biomolecule is bonded on the surface of the silica particles, wherein the silica particles having a thiol group on a surface thereof are produced by a method comprising:

forming silica particles having bound water on the surface by allowing hydrolysis and polycondensation of one kind or two or more kinds of silane compounds in an aqueous ammonia-containing solvent to form a siloxane bond;

washing the silica particles having bound water on the surface with a hydrophilic organic solvent to remove free water other than the bound water existing on the surface of the silica particles; and mixing the silica particles having bound water on the surface and a silane coupling agent having a reactive functional group including a thiol group; in an organic solvent to hydrolyze the silane coupling agent by the bound water existing on the surface of the silica particles.

\* \* \* \* \*